(12) United States Patent
Matsui et al.

(10) Patent No.: US 6,535,287 B1
(45) Date of Patent: Mar. 18, 2003

(54) COLOR IDENTIFYING DEVICE

(75) Inventors: Toshihisa Matsui, Ishikawa-ken (JP); Yoshikatsu Hifumi, Ishikawa-ken (JP); Yasunori Touma, Ishikawa-ken (JP); Shinya Hashizume, Ishikawa-ken (JP); Hideaki Ariya, Ishikawa-ken (JP)

(73) Assignee: KabushikiKaisha Hokkeikougyou, Kanazawa (JP)

( * ) Notice: Subject to any disclaimer, the term of this patent is extended or adjusted under 35 U.S.C. 154(b) by 113 days.

(21) Appl. No.: 09/671,838

(22) Filed: Sep. 27, 2000

(30) Foreign Application Priority Data

Jul. 7, 2000 (JP) ......................................... 2000-206320

(51) Int. Cl.⁷ ................................................. G01J 3/51
(52) U.S. Cl. ...................... 356/406; 356/425; 356/419; 250/226
(58) Field of Search ................................ 356/402, 405, 356/406, 407, 416, 419, 425; 250/226

(56) References Cited

U.S. PATENT DOCUMENTS 4,259,020 A * 3/1981 Babb ........................... 356/407

FOREIGN PATENT DOCUMENTS

| DE | 4400021 A1 | * | 7/1995 |
| EP | 0114515 | * | 8/1984 |
| EP | 0235460 | * | 9/1987 |
| JP | 56-137235 | * | 10/1981 |
| JP | 63-163120 | * | 7/1988 |

* cited by examiner

Primary Examiner—F. L. Evans
(74) Attorney, Agent, or Firm—Flynn, Thiel, Boutell & Tanis, P.C.

(57) ABSTRACT

Difficulty recognizing colors which a sight-impaired person has is solved by a color identifying device of the invention comprising a means for identifying a color by comparing data measured by color sensor 4a and stored reference data and a means for externally outputting the color identified by the color identifying means by a voice, wherein a measurement aperture portion is pressed against the surface of an object the color name of which a sight-impaired person desires to know, light (of three RGB types) reflected from the object is measured by the measurement portion 4, the measured data is transmitted to the color identifying means, the program within the color identifying means calculates the measured data and compares the calculated data with the reference data (table data) which is systematically classified, the color name of the measured data is selected, and the color name (the basic color name, lightness, chroma and hue) of the object is outputted from speaker 28 by a voice.

15 Claims, 17 Drawing Sheets

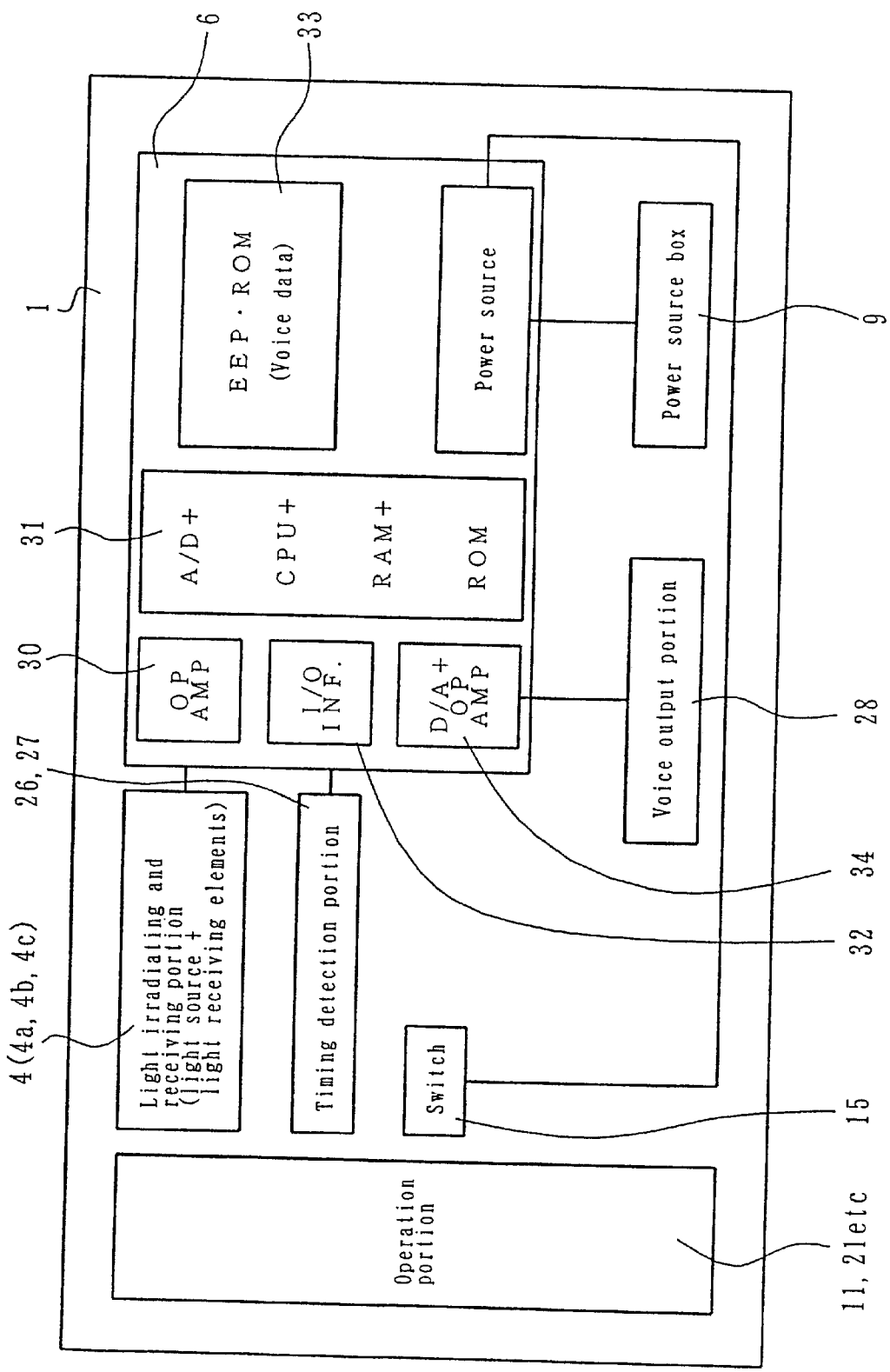

Names of Basic Chromatic Colours

| Romanized Japanese | English Equivalent (informative reference) | Abbreviated symbol (informative reference) |
|---|---|---|
| AKA | red | R |
| KIAKA | orange, yellow red | O |
| KI | yellow | Y |
| KIMIDORI | yellow green, green yellow, leaf green | L |
| MIDORI | green | G |
| AOMIDORI | blue green, cyan | C |
| AO | blue | B |
| AOMURASAKI | violet, purple blue | V |
| MURASAKI | purple | P |
| AKAMURASAKI | red purple, magenta | M |

Note ([1]) KI may be made KIIRO.
Remark: The name of basic chromatic colour shall be used as the name of hlue, and the and the mutual relation of the hues is shown in Fig. 1.

(JIS Z 8102 Table 1)

(b)

Basic Names of Achromatic Colours

| Romanize Japanese | English Equivalent (informative reference) | Abbreviated symbol (informative reference) |
|---|---|---|
| SHIRO | white | W |
| HAIIRO | (neutral) grey (English), (neutral) gray (American) | N |
| KURO | black | S ([2]) |

Note ([2]) S is the abbreviation of Schwarz (German).

(JIS Z 8102 Table 2)

FIG. 5

Modifiers concerning Lightness and Chroma of Chromatic Colours

| Romanized Japaneze | English Equivalent (informative reference) | Abbreviated symbol (informative reference) |
|---|---|---|
| AZAYAKANA | vivid | vv |
| AKARUI | lgiht | lt |
| KOI | deep | dp |
| USUI | pale | pl |
| KUSUNDA | dull | dl |
| KURAI | dark | dk |
| GOKUUSUI | very pale | vp |
| AKARUIHAI | light greyish (English), light grayish (American) | lg |
| HAI | greyish (English), grayish (American) | mg |
| KURAIHAI | dark greyish (English), dark grayish (American) | dg |
| GOKUKURAI | very dark | vd |

(JIS Z 8102 Table 3)

FIG. 6

Modifiers concerning Hue

| Romanized Japanese | Applicable basic names of colours | English Equivalent (informative reference) | Abbreviated symbol (informative reference) |
|---|---|---|---|
| AKAMINO | Purple, yellow, white, (neutral) grey, black | reddish | r |
| KIMINO | Red, green, white, (neutral) grey, black | yellowish | y |
| MIDORIMINO | Yellow, blue, white, (neutral) grey, black | greenish | g |
| AOMINO | Green, purple, white, (neutral) grey, black | bluish | b |
| MURASAKIMINO | Blue, red, white, (neutral) grey, black | purplish | p |

Examples: reddish yellow, yellowish red, greenish blue, reddish grey (JIS Z 8102 Table 5)

FIG. 7

Relationships between RGB data, HLS data, and color names

| | R | G | B | Hue | Light | Satu | Angle | Color name |
|---|---|---|---|---|---|---|---|---|
| Test sample 1 DIC 549 1/2 | 126 | 121 | 104 | 5 | 12 | 2 | 46 | Grey |
| Test sample 2 DIC 569 | 255 | 212 | 0 | 5 | 11 | 20 | 49 | Vivid reddish yellow |
| Black test sample | 22 | 22 | 17 | 6 | 19 | 3 | 60 | Black |
| White test sample | 231 | 228 | 235 | 16 | 2 | 5 | 258 | White |
| Red | 182 | 22 | 29 | 2 | 13 | 16 | 357 | Red |
| Blue | 31 | 45 | 202 | 14 | 11 | 15 | 235 | Blue |
| Green | 57 | 181 | 25 | 10 | 13 | 16 | 107 | Green |

FIG. 8
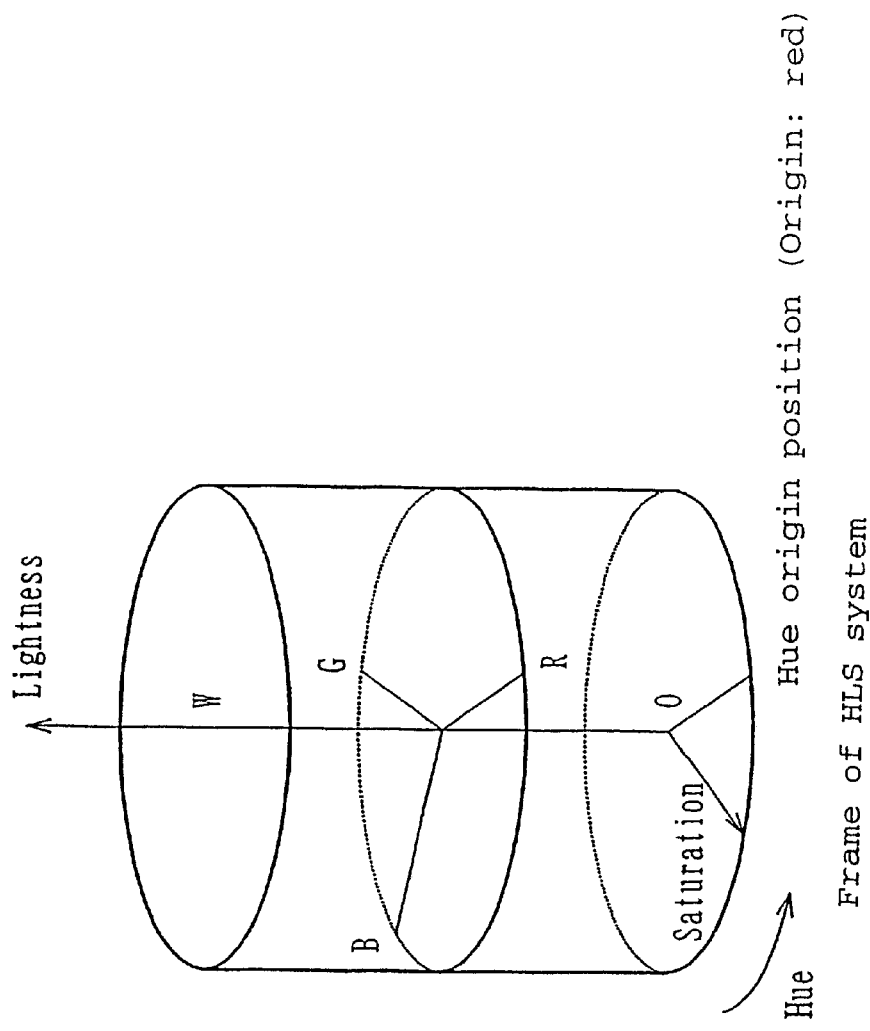
Frame of HLS system
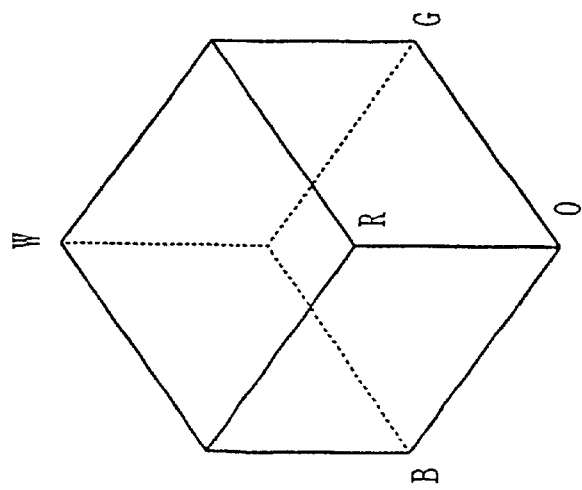
Frame of RGB system

Mutual Relation of Modifiers concerning Hue (JIS Z 8102 Fig. 3)

Division of Hue Circle (JIS Z 8721 Fig. 1)

2.5R - 10RP: JIS standards
1 - 20: Present invention

FIG. 12

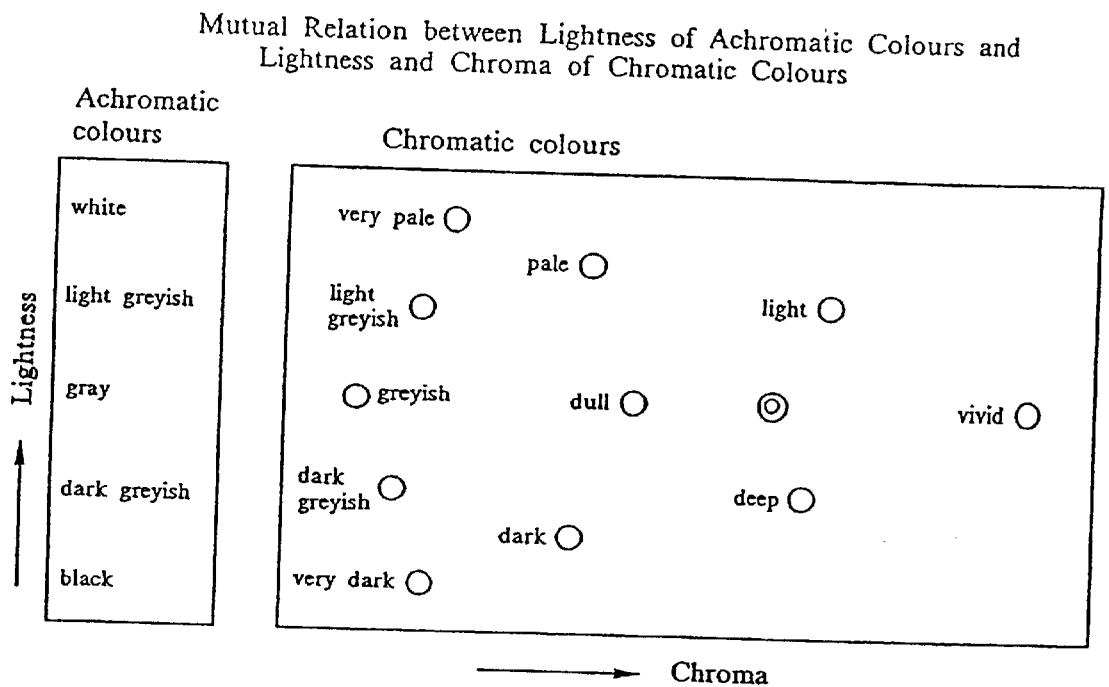

Mutual Relation between Lightness of Achromatic Colours and Lightness and Chroma of Chromatic Colours Remarks 1. ○ mark expresses the basic name of colour indicated in Table 1.

Example: very red, dark greyish green, light purple.

2. ◎ mark expresses only the basic name of colour indicated in Table 1 without using modifier.

3. In the case where subdivision is not required, the modifier only of bold characters shall be used.

4. For the euphony of the Japanese terms, "i" may be omitted from the modifier usui for the color names marked with    as shown in Examples.

Examples: usuaka, usumidori, usuao, usumurasaki (JIS Z 8102  Fig. 2)

(JIS Z 8721 Fig. 2)

Relation between Specification by Three Attributes of Colour and Systematic Name of Colour Reddish Yellow (7 YR to 2 Y, excl.)

(JIS Z 8102 Attached Fig. 5)

FIG. 15

Relationship between color table number and hue angle

| Color table No. | 1 | 2 | 3 | 4 |
|---|---|---|---|---|
| Hue angle (H) | 328<H≦351 | 351<H≦9 | 9<H≦25 | 25<H≦40 |
| Color table No. | 5 | 6 | 7 | 8 |
| Hue angle (H) | 40<H≦50 | 50<H≦60 | 60<H≦70 | 70<H≦80 |
| Color table No. | 9 | 10 | 11 | 12 |
| Hue angle (H) | 80<H≦105 | 105<H≦145 | 145<H≦170 | 170<H≦190 |
| Color table No. | 13 | 14 | 15 | 16 |
| Hue angle (H) | 190<H≦215 | 215<H≦240 | 240<H≦250 | 250<H≦260 |
| Color table No. | 17 | 18 | 19 | 20 |
| Hue angle (H) | 260<H≦270 | 270<H≦282 | 282<H≦305 | 305<H≦328 |

FIG. 16

Values of lightness (L) and chroma (S)

| 1 | 2 | 3 | 4 |
|---|---|---|---|
| 0.00≦S<1.00 | 1.00≦S<2.00 | 2.00≦S<3.00 | 3.00≦S<4.00 |
| 5 | 6 | 7 | 8 |
| 4.00≦S<5.00 | 5.00≦S<6.00 | 6.00≦S<7.00 | 7.00≦S<8.00 |
| 9 | 10 | 11 | 12 |
| 8.00≦S<9.00 | 9.00≦S<10.00 | 10.00≦S<11.00 | 11.00≦S<12.00 |
| 13 | 14 | 15 | 16 |
| 12.00≦S<13.00 | 13.00≦S<14.00 | 14.00≦S<15.00 | 15.00≦S<16.00 |
| 17 | 18 | 19 | 20 |
| 16.00≦S<17.00 | 17.00≦S<18.00 | 18.00≦S<19.00 | 19.00≦S |

Note: When the lightness (L) is calculated, S=L (substitute L for S).

FIG. 17

L-S table of hue 5 (reddish yellow)

Lightness(L) ↓

| L \ S | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| 1  | 1 | 1 | 6 | 6 |    |    |    |    |    |    |    |    |    |    |    |    |    |    |    |    |
| 2  | 1 | 1 | 6 | 6 | 11 | 11 | 11 | 11 |    |    |    |    |    |    |    |    |    |    |    |    |
| 3  | 1 | 1 | 6 | 6 | 11 | 11 | 11 | 11 |    |    |    |    |    |    |    |    |    |    |    |    |
| 4  | 1 | 1 | 6 | 6 | 11 | 11 | 11 | 11 | 16 | 16 | 16 | 16 |    |    |    |    |    |    |    |    |
| 5  | 2 | 2 | 7 | 7 | 12 | 12 | 12 | 12 | 16 | 16 | 16 | 16 |    |    |    |    |    |    |    |    |
| 6  | 2 | 2 | 7 | 7 | 12 | 12 | 12 | 12 | 16 | 16 | 16 | 16 | 19 | 19 | 19 | 19 |    |    |    |    |
| 7  | 2 | 2 | 7 | 7 | 12 | 12 | 12 | 12 | 16 | 16 | 16 | 16 | 19 | 19 | 19 | 19 |    |    |    |    |
| 8  | 2 | 2 | 7 | 7 | 12 | 12 | 12 | 12 | 17 | 17 | 17 | 17 | 19 | 19 | 19 | 19 | 22 | 22 | 22 | 22 |
| 9  | 3 | 3 | 8 | 8 | 13 | 13 | 13 | 13 | 17 | 17 | 17 | 17 | 19 | 19 | 19 | 19 | 22 | 22 | 22 | 22 |
| 10 | 3 | 3 | 8 | 8 | 13 | 13 | 13 | 13 | 17 | 17 | 17 | 17 | 20 | 20 | 20 | 20 | 22 | 22 | 22 | 22 |
| 11 | 3 | 3 | 8 | 8 | 13 | 13 | 13 | 13 | 17 | 17 | 17 | 17 | 20 | 20 | 20 | 20 | 22 | 22 | 22 | 22 |
| 12 | 3 | 3 | 8 | 8 | 13 | 13 | 13 | 13 | 17 | 17 | 17 | 17 | 20 | 20 | 20 | 20 | 22 | 22 | 22 | 22 |
| 13 | 4 | 4 | 9 | 9 | 14 | 14 | 14 | 14 | 17 | 17 | 17 | 17 | 20 | 20 | 20 | 20 | 22 | 22 | 22 | 22 |
| 14 | 4 | 4 | 9 | 9 | 14 | 14 | 14 | 14 | 17 | 17 | 17 | 17 | 21 | 21 | 21 | 21 | 21 |    |    |    |
| 15 | 4 | 4 | 9 | 9 | 14 | 14 | 14 | 14 | 18 | 18 | 18 | 18 | 21 | 21 | 21 | 21 | 21 |    |    |    |
| 16 | 4 | 4 | 9 | 9 | 14 | 14 | 14 | 14 | 18 | 18 | 18 | 18 | 21 | 21 | 21 | 21 | 21 |    |    |    |
| 17 | 5 | 5 | 10 | 10 | 15 | 15 | 15 | 15 | 18 | 18 | 18 | 18 |    |    |    |    |    |    |    |    |
| 18 | 5 | 5 | 10 | 10 | 15 | 15 | 15 | 15 |    |    |    |    |    |    |    |    |    |    |    |    |
| 19 | 5 | 5 | 10 | 10 | 15 | 15 | 15 | 15 |    |    |    |    |    |    |    |    |    |    |    |    |
| 20 | 5 | 5 | 10 | 10 |    |    |    |    |    |    |    |    |    |    |    |    |    |    |    |    |

Saturation(S) →

FIG. 18

LS values of hue 5 (reddish yellow) and color names

| LS value | Color name |
| --- | --- |
| 1 | white |
| 2 | light grey |
| 3 | grey |
| 4 | dark grey |
| 5 | black |
| 6 | yellowish white |
| 7 | light yellowish grey |
| 8 | yellowish grey |
| 9 | dark yellowish grey |
| 10 | yellowish black |
| 11 | very pale yellow |
| 12 | light greyish yellow |
| 13 | greyish yellow |
| 14 | dark greyish |
| 15 | very dark yellow |
| 16 | pale reddish yellow |
| 17 | dull reddish yellow |
| 18 | dark reddish yellow |
| 19 | light reddish yellow |
| 20 | reddish yellow |
| 21 | deep reddish yellow |
| 22 | vivid reddish yellow |

COLOR IDENTIFYING DEVICE

BACKGROUND OF THE INVENTION

1. Field of the Invention

The present invention relates to a color identifying device being able to be utilized by, for example, a sight-impaired person, which enables said sight-impaired person to identify (judge or recognize) the color of an object by judging the color of the substance and outputting the name of the color by a voice with said device brought into contact with the surface of the substance (object) whose color said person wants to know.

2. Description of the Related Art

Conventionally, it was difficult for a person who has difficulty identifying or recognizing the color of an object, like a sight-impaired person, to identify or recognize colors unless he or she is given explanation from a third person who is able to identify the colors or any explanation thereof is given by any other means such as Braille, etc.

Further, even though the sight-impaired person receives an explanation of the colors, there were limits on explaining an infinite variety of color names whose hues or tints such as lightness, etc., differ from each other.

Also, a sight-impaired person is eager to know colors in his or her daily life, without any assistance of a helper, with a view to coordinating his or her own clothes, wearing socks of the same color on his or her own feet, or classifying empty bottles by colors for discharge to a collection station.

However, no device exists, which is suitable for assisting a sight-impaired person to identify or recognize colors, and there were various types of inconveniences sight impaired people experienced.

SUMMARY OF THE INVENTION

The present invention provides a color identifying device which is able to read the names of colors of a substance and transmit the color name by a voice by only bringing the invention into contact with the surface of the substance.

The invention is a color identifying device developed in view of the abovementioned problem based on the prior art, which is the difficulty a sight-impaired person experiences to identify or recognize the colors, and the color identifying device is provided with a means for judging color by comparing data measured by the light receiving elements with stored reference data; and the outputting means is made into a means for peripherally outputting color, which is judged and identified by the color identifying means, by a voice, wherein, as a measurement aperture portion is brought into contact with the surface of a substance (object) whose color the sight-impaired person wants to know, the measurement portion measures light (three types of RGB) reflected from the substance, transmits the measured data (RGB data) to a color identifying means, the measured data are calculated by programs stored in the color identifying means, the corresponding calculated data (HIS data) are compared with the systematically classified reference data (table data), the color name of the measured data is selected therefrom, and the color name (the basic color name, lightness, chroma and hue) of the substance is outputted by a voice.

And, since the measurement portion is provided with a white light source which emits white light to the object and three primary color light receiving elements which receive the light reflected from the object, the measurement of the reflected light is carried out by three types of primary colors (RGB), the calculation comparison is carried out in the form of HIS, and the selection of the color name is carried out on the basis of the human sense of sight.

Further, a self-proof (correction) circuit is incorporated. For example, the circuit is provided with a means for disposing and removing a proof test sample of a specified color between the measurement portion and an object with respect to deterioration and disorder of respective parts due to continuous use of the color identifying device, and changes in the environment when used, and a means for carrying out a self-proof by comparing the measured data of the proof test sample with the reference data, whereby the device can be used in a stabilized state, and a sight-impaired person can use it with his or her mind at ease. Thereby, the abovementioned problem can be solved.

In short, according to the invention, since the measurement portion 4, color identifying means, and output means (speaker 28) are provided, by contacting the color identifying device packaged as one unit with the surface of an object the color name of which a sight-impaired person desires to know, the color of the object is identified and the color name is outputted by a voice, whereby the sight-impaired person can recognize (identify) the color of the object.

In addition, since the measurement portion 4 is provided with white light sources 4b and 4c for irradiating white light to an object and three primary color light receiving elements for receiving light reflected from the object (color sensor 4a), a reliable optical system with a simple structure can be achieved, and since the color identifying means is provided with a means which compares data measured by the light receiving elements and the stored reference data to identify a color, by color comparison, a color can be easily identified in a short time (instantly).

Furthermore, since the output means is arranged so as to externally output the color identified by the color identifying means by a voice, a sight-impaired person can recognize the color name by the voice.

Furthermore, since the measured data is RGB data, measurement can be easily carried out by the light receiving elements of the three primary colors, and also, since HLS data is calculated from the RGB data, and the HLS data have commonality with the generally known Munsell hue ring, there is the reality that the HLS data and the indication of the data can be stabilized, and in addition, since the HLS data and the stored reference data are compared with each other, a color can be easily identified.

As the light receiving elements of the three primary colors, since photoelectric conversion elements having sensitivity with respect to the three primary colors are provided, the measured RGB data can be easily measured by the photoelectric converting elements, and in addition, since three photo diodes provided with three types (RGB) of filters are provided as photoelectric converting elements, by only attaching the filters to the photo diodes, the RGB data can be easily measured.

Furthermore, since a moving means for disposing and removing a proof test sample of a specified color is provided between the measurement portion 4 and an object, arrangement in the device and measurement of the proof test sample to be used for self-proofing can be easily carried out, and in addition, since a means which compares the measured data of the proof test sample and the reference data of the proof test sample to carry out self-proofing is provided, even if aging deterioration of the power source and various components occurs, or in accordance with changes in environment of use, measurements and color identification can be carried out by means of self-proofing.

Furthermore, black test sample 23 or white test sample 24 is used as a proof test sample of a specific color, the proof test sample generally has the three primary colors, and individual data of the three types of RGB is used as a proof data, whereby proofing of the three types of RGB can be simultaneously carried out. In addition, since one to three of three-primary color samples are used as a proof test sample of a specific color, the maximum value data or low value data is measured, and the middle value is not defined as a reference, proofing can be accurately carried out.

Furthermore, since the measured data of an object is proofed by means of self-proofing, proofing can be made to accord to each environment of use.

Furthermore, a means for moving, measuring, and removing the proof test sample by the operation of the switch 7 to achieve automatic measurement of an object is provided between the measurement portion 4 and the object, thus proofing and measurements can be automatically and successively carried out.

Furthermore, since a measurement aperture portion 3 is opened in the mainframe case 1 so that the proof test sample and space is moved inside said measurement aperture portion 3 in order, the operations of proofing and measurements are carried out inside, the movement of the color identifying device with respect to an object becomes unnecessary, whereby proofing and color identification can be made by a simple contacting operation.

Furthermore, the moving means is constructed such that a rotary disk (measurement base plate 21) is provided with a proof test sample and a measuring window 25 being a space, and said rotary disk is devised so as to intermittently move, and thus the space for components required to carry out proofing can be reduced, and the color identifying device can be reduced in size.

Furthermore, since the speaker 28 is installed as a means for externally outputting a voice, the color identifying means and output means can be packaged as one unit and made easier in operation, and in addition, an earphone is provided as a means for externally outputting a voice, whereby a voice does not leak externally, whereby the color identifying device can be used regardless of the surrounding environment.

BRIEF DESCRIPTION OF THE DRAWINGS

The foregoing and other features and advantages of the present invention will become more readily more appreciated as the same becomes better understood by reference to the following detailed description when taken into conjunction with the accompanying drawings wherein:

FIG. 3 is a diagram showing the circuitry.

FIG. 4 is a list of basic color names.

FIG. 5 is a list of modifiers with regard to the lightness and chroma.

FIG. 6 is a list of modifiers with regard to the hue.

FIG. 7 is a table showing the relationships between the measured RGB data, converted HLS data, and selected color names.

FIG. 8 is a drawing showing the frame of reference of the RGB color space and the frame of reference of the HLS color space.

FIG. 12 is a drawing showing correlation between the lightness of achromatic colors and lightness and chroma of chromatic colors.

FIG. 15 is a table (standard data) stored in the ROM of the control circuit board, which show the relationship between the color table numbers and hue angles.

FIG. 16 is a table (reference data) stored in the ROM of the control circuit board, which shows the relationship between the calculated values of the lightness and hue.

FIG. 17 is a table (reference data) stored in the ROM of the control circuit board, which shows the relationship between the lightness, hue, and LS value.

FIG. 18 is a drawing showing the relationship between the LS value and color name.

DETAILED DESCRIPTION OF THE PREFERRED EMBODIMENT

Hereinafter, a description is given of an embodiment of the invention with reference to the accompanying drawings.

A color identifying device according to the invention is brought into contact with the surface of a substance whose color name (basic color name, lightness, chroma, and hue) a sight-impaired person wants to know, the measurement portion in the color identifying device emits and receives light and measures light reflected from the substance (to obtain its RGB data), wherein the measured data are transmitted to a color identifying means, the program in the color identifying means calculates three types of HLS from the measured data, the HLS calculated data are compared with the systematically classified reference data (table data), the color name of the RGB measured data is selected, that is, the color name of the substance (object) is identified, and the color name is outputted by a voice, and the sight-impaired person is allowed to identify or recognize the color name of the substance.

Hereinafter, a description is given of the detail of the color identifying device.

Figure 1:
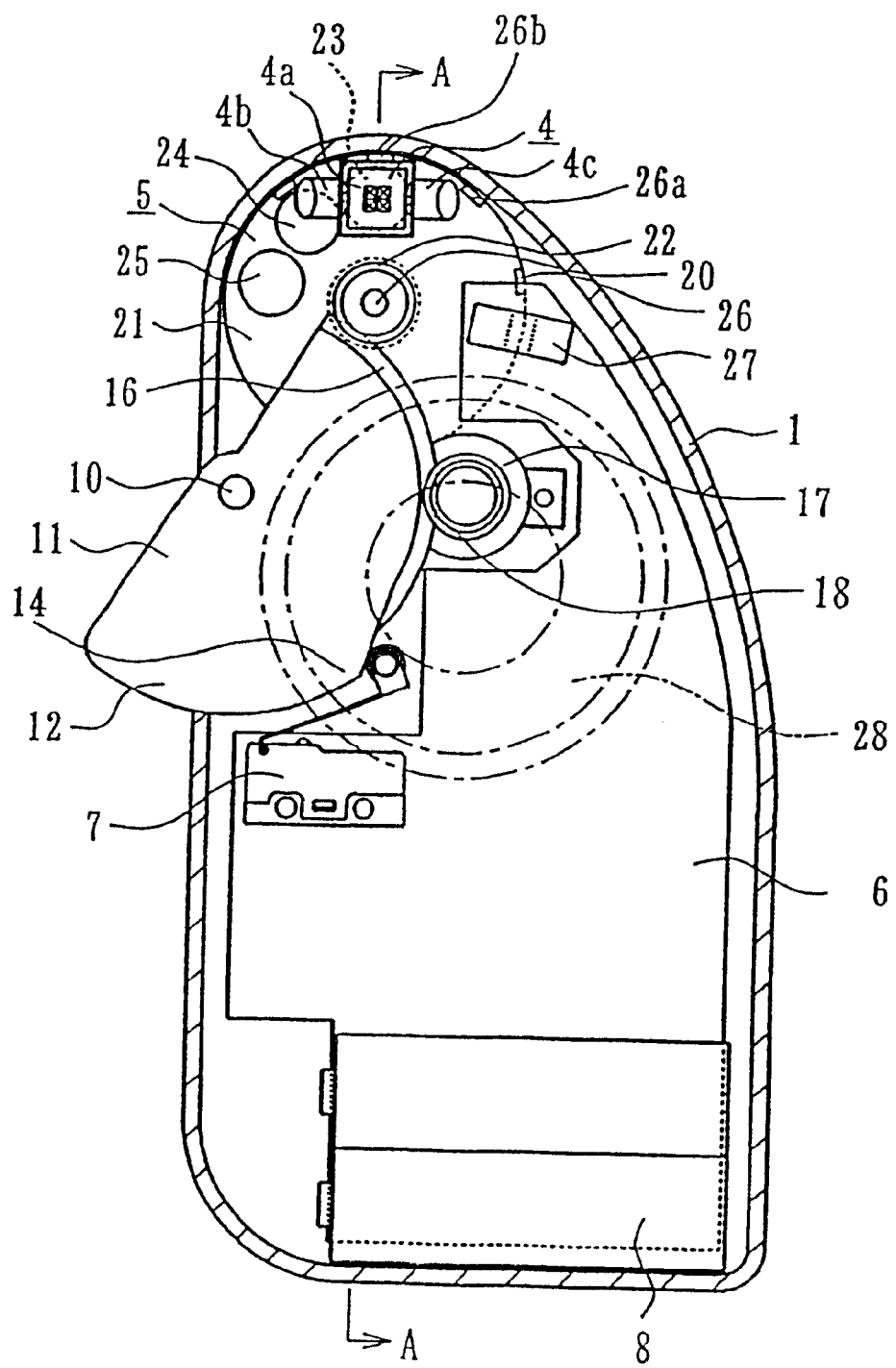
FIG. 1 is a partial sectional plan view showing the internal structure of the color identifying device relating to the invention.
Figure 2:
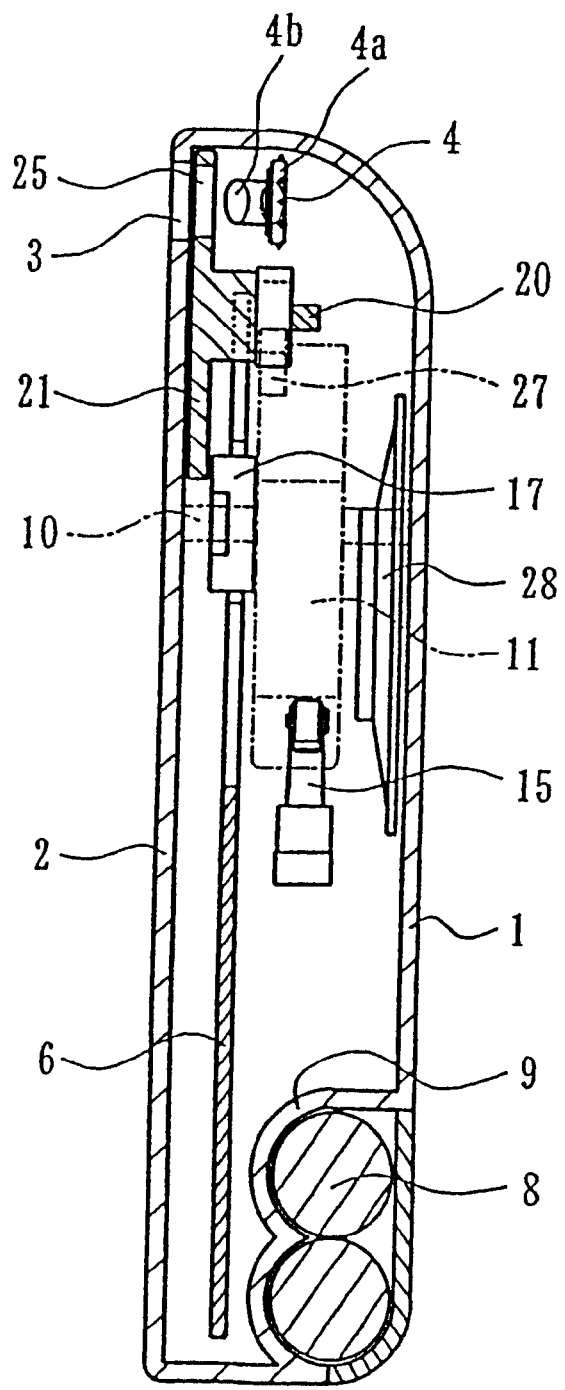
FIG. 2 is a sectional view along the A—A line of FIG. 1.

As shown in FIG. 1 and FIG. 2, a measurement aperture portion 3 is provided on the bottom plate 2 of a flat mainframe case or housing 1, and a measurement portion 4 which irradiates, emits and receives light with respect to the object, passing through the measurement aperture portion 3 is provided inside the mainframe case 1 corresponding to the measurement aperture portion 3.

In addition, a proofing means 5 is secured between the measurement aperture portion 3 and the measurement portion 4, and at the same time, components such as a control circuit board 6, a switch 7, etc., are incorporated in the mainframe case Also, a power source box 9 is provided on the upper part of the mainframe case 1, which can detachably accommodate a dry battery 8.

The measurement portion 4 which irradiates and receives light has a color sensor 4a, in which three primary color light receiving elements are packaged as one unit, disposed at an upper position opposed to the measurement aperture portion 3 secured on the bottom plate 2, and has two white light sources 4b and 4c inclined by 45 degrees and disposed at both sides of the corresponding color sensor 4a.

As one example of the three primary color light receiving elements employed for the color sensor 4a, three photo diodes (photoelectric converting elements) provided with three types of filters (RGB) so that the maximum sensitivity wavelength becomes 660 nm for RED, 540 nm for GREEN, and 460 nm for BLUE, and are able to separately measure the three primary color incident light intensities (light receiving amount) by photodiodes having sensitivity for the three primary colors.

Also, since two white light sources 4b and 4c are provided, a necessary amount of light can be secured in the light source, and also the white light sources 4b and 4c are inclined by 45 degrees. This is because white light is irradiated onto an object, passing through the measurement aperture portion 3, the light reflected from the object is received by the color sensor 4a, and accuracy of color measurement (measured data) is improved with respect to disordered reflection from the object.

Hereinafter, a description is given of a detailed example.

A switch matrix axis 10 is secured in the upper and lower direction of the mainframe case 1, and a semi-circular switch base plate 11 is rotatably attached to the corresponding switch matrix axis 10, and a fan-shaped pressing portion 12 consisting of a half of the arcuate portion of the switch base plate 11 and a part of a semi-circle is caused to protrude from the mainframe case 1 so that the half of the arcuate portion of the corresponding switch base plate 11 protrudes so as to be pressed in, thereby constituting a lever switch 7.

The ends of a pair of twist springs (not illustrated) that are partially wound on the switch matrix axis 10 are attached to the bottom plate 2, and the other ends thereof are attached to the switch base plate 11, whereby the switch base plate 11 once turned can be automatically reset.

Also, a protrusion type (gap-like) switch drive portion 14 is formed at the semi-circular portion of the switch base plate 11 accommodated in the mainframe case 1, and simultaneously, a switch arm 15 is provided at the controlling printed circuit board 6 secured in the mainframe case 1, wherein by causing the switch drive portion 14 and the switch arm 15 to be brought into contact with each other (to be pressed by the step) by movement of the switch base plate 11, the switch arm 15 is inclined and is turned on.

In addition, while a spur gear (rack) 16 is provided at the outer circumferential portion of a part of the semicircular portion of the switch base plate 11, a damper 17 for adjusting the lever speed is provided at the outer position opposed to the spur gear, wherein a spur gear 18, secured at the outer circumferential edge of the corresponding damper 17, is engaged in the spur gear 16 of the switch base plate 11.

In the construction, by pressing and operating the protruded fan-shaped pressing portion 12 of the mainframe case 1 at the switch base plate 11, the switch is turned on, and at the same time, the turning speed of the switch base plate 11 is decelerated by engagement of the switch base plate 11 with the damper 17.

Also, a measurement matrix axis 20 is provided at the position opposed to the tip end side of the spur gear 16 of the switch base plate 11, a disk-shaped measurement base plate 21 is rotatably provided at the corresponding measurement matrix axis 20, and a spur gear 22 is attached to the measurement matrix axis 20 in such a state where it is fixed along with the measurement base plate (rotary disk 21), wherein the spur gear 22 of the measurement base plate 21 is engaged with the spur gear 16 of the switch base plate 11.

By the construction, the measurement base plate 21 is caused to rotate in response to the switch base plate 11 which rotates at a low speed by actions of the damper 17.

Further, the measurement base plate 21 is disposed between the measurement aperture portion 3 and the measurement portion 4 while a black test sample 23 and a white test sample 24, which are proof test samples of specified colors, and a measurement window 25 being a space are provided at appointed positions on the measurement base plate 21.

Also, dogs 26, 26a and 26b, respectively, corresponding to the black test sample 23, white test sample 24 and measurement window 25 are provided on the outer circumferential edge at the other side of the measurement base plate 21. And, a timing detection sensor 27 which detects the dogs 26, 26a and 26b is provided on the controlling printed circuit board 6.

By the construction, the black test sample 23, white test sample 24, measurement window 25, dogs 26, 26a and 26b are rotated and moved by rotation of the switch base plate 11 and measurement base plate 21, and when the black test sample 23 is located between the measurement portion 4 and the measurement aperture portion 3, the light reflected from the black test sample 23 is measured at the detection timing of the dog 26, and next the light reflected from the white test sample 24 is measured at the detection timing of the dog 26a, and a self-proof is carried out as described below.

Also, when the measurement window 25 is located between the measurement portion 4 and the measurement aperture portion 3, light passes through the measurement window (space) 25 at the detection timing of the dog 26b, the light reflected therefrom is measured, and the color of a substance is identified.

Further, a speaker 28 is incorporated in the mainframe case 1 as a means for peripherally outputting an identified color of a substance (object) by a voice. However, an earphone (including its terminal) (not illustrated) may be employed instead of the speaker 28.

Next, a circuit (means), in which a controlling printed circuit board 6 is provided, is described below.

As shown in FIG. 3, the abovementioned movable components (switch base plate 11, measurement base plate 21, etc.,), a controlling printed circuit board 6 which takes a role of a color identifying means is incorporated in the mainframe case 1 in addition to the light irradiating and receiving portion, timing detection portion, switch, a voice outputting portion, and a power source portion.

The major part in which the controlling printed circuit board 6 is mounted is constructed of a CPU, a RAM, a ROM, an A/D, etc. Hereinafter, a description is given of the features and actions thereof.

Measured (analog) data of the light irradiating and receiving portion (color sensor 4a, and white light sources 4b and 4c) are amplified by an operational amplifier OP AMP 30 at the input side, and are transmitted to the main circuit 31. And, timing data of the timing detection portion (dogs 26, 26a and 26b, and sensor 27) are transmitted to the main circuit 31 via an input/output INF. 32.

The main circuit 31 specifies the measured (analog) data from the operational amplifier 30 corresponding to the timing data transmitted from the input/output INF. 32, and are converted from analog to digital by an A/D converter.

And, the color is identified from the RGB data of the measured (digital) data on the basis of calculation equations stored in a ROM and reference data (table data in FIG. 15 through FIG. 18), etc.

Three types (or one or two types for some color names) of voice (digital) data are extracted from an EEP-ROM 33 based on the color identification, and the voice (digital) data are transmitted from the main circuit 31 to an operational amplifier at the output side.

And, after the voice (digital) data are converted to analog by a digital/analog converter, the voice signals amplified by an operational amplifier 34 is transmitted to the speaker 28 from which the voice is outputted.

Next, a description is given of actions of a color identifying device according to the present invention.

As the power source of a color identifying device is turned on by pressing and turning the switch base plate 11, the measurement portion 4 is driven or started (that is, receives light); and the measurement base plate 21 is caused to rotate at a low speed, whereby the black test sample 23, white test sample 24 and measurement window 25 are gradually moved in between the measurement portion 4 and the measurement aperture portion 3.

When the black test sample 23, etc., is located at the corresponding measurement position, the sensor 27 detects the dogs 26, 26a and 26b, wherein the data of the light received (measured) of the color sensor 4a at that time are transferred to the controlling printed circuit board 6.

That is, when white light irradiated from the white light sources 4b and 4c is reflected from the proof test samples, or when it is reflected from a substance (object) (passing through the measurement window 25 along with the irradiating and receiving light), light of a specified wavelength in response to the proof test samples or the substance (object) is reflected, and the measured value photoelectrically converted in response to the light receiving quantity of the three primary colors, which is received by the color sensor 4a, is transferred to the controlling printed circuit board 6.

Subsequently, the measured data (RGB data) are calculated and converted to calculated data (HLS data) in the controlling printed circuit board 6 to which the measured data are transferred, and the color name of the substance is selected based on the HLS data.

Also, the color name of the substance is expressed in terms of three categories, i.e. basic color name, modifier regarding the lightness and chroma and modifier regarding the hue, which are in compliance with the Japanese Industrial Standards (JIS standards).

After voice data of the basic color name and two types of modifiers, which are selected from the HIS data in compliance with the JIS standards, are extracted, the voice data are transferred to the speaker 28, whereby the voice data are spoken to allow a sight-impaired person to hear and identify or recognize the color of the substance.

Hereinafter, a description is given of the relationship between the human sense of sight and the present invention, the relationship between the human sense of sight and the JIS standards regulation (Z 8102, etc.), the relationship between the JIS standards regulation and the HLS data, the relationship between the RGB data of measured data and the HLS data of calculated data, and the system for selecting the color names from the measured data, etc., and finally a description is given of the proofing system.

First, a description is given of the relationship between light beam reflection of a substance and the basic principle of human color perception, and the relationship between the human sense of sight and the present invention.

When white light consisting of the three primary colors (Red:R, Green:G and Blue:B) is irradiated onto an object, the object (substance) can reflect a larger amount of light having a specified wavelength of a visible light beam, and absorb a larger amount of light having a specified wavelength thereof.

That is, the relative amount which relates to which part of the visible light can be reflected, or which part thereof is absorbed therein may differ according to substances, and humans recognize colors (visible light beams) reflected from a substance and can identify the colors.

And, although, in the invention, the colors are identified after the reflected light is numerically measured, the color identification made by humans is different from the color identification method of the invention.

That is, humans identify colors based on the sense of sight (total of the sense of sight for the three primary colors) led from the light reflected from the substance and the sensitivity of eyes.

Also, the sense of sight for each of the three primary colors and the total sense of sight of the three primary colors can be calculated as an integral value on the basis of the reflection index per wavelength and the part where the sensitivities of eyes overlap each other.

On the contrary, in the invention, after the reflected light of the three primary colors (RGB) is measured, and the measured RGB data are converted to calculated HLS data, the HLS data are applied to table data in compliance with the JIS standards, wherein three attributes (hue, chroma, and lightness) of color perception, which are regulated in the JIS standards described later, are obtained, voice data of the color name (basic color name, lightness, chroma, and hue) are extracted and the color is outputted by a voice.

And, the JIS standards exists as a means of expressing the sense of sight (color identification) of a human.

The expression of color names which are transmitted to a sight-impaired person by measuring a substance (object), that is, the three attributes (hue, lightness and chroma) of color perception are employed on the basis of the expression regulated in compliance with the JIS standards "Color names of substances" (Z 8102).

That is, as shown in the names of basic chromatic and achromatic colors in FIG. 4(a) and FIG. 4(b), the basic colors names of a substance are expressed in terms of thirteen types consisting of chromatic colors and achromatic colors, and at the same time, all the colors are expressed by a combination of the basic chromatic and achromatic colors and two types of modifiers indicated in Tables of modifiers shown in FIG. 5 and FIG. 6.

Figure 9:
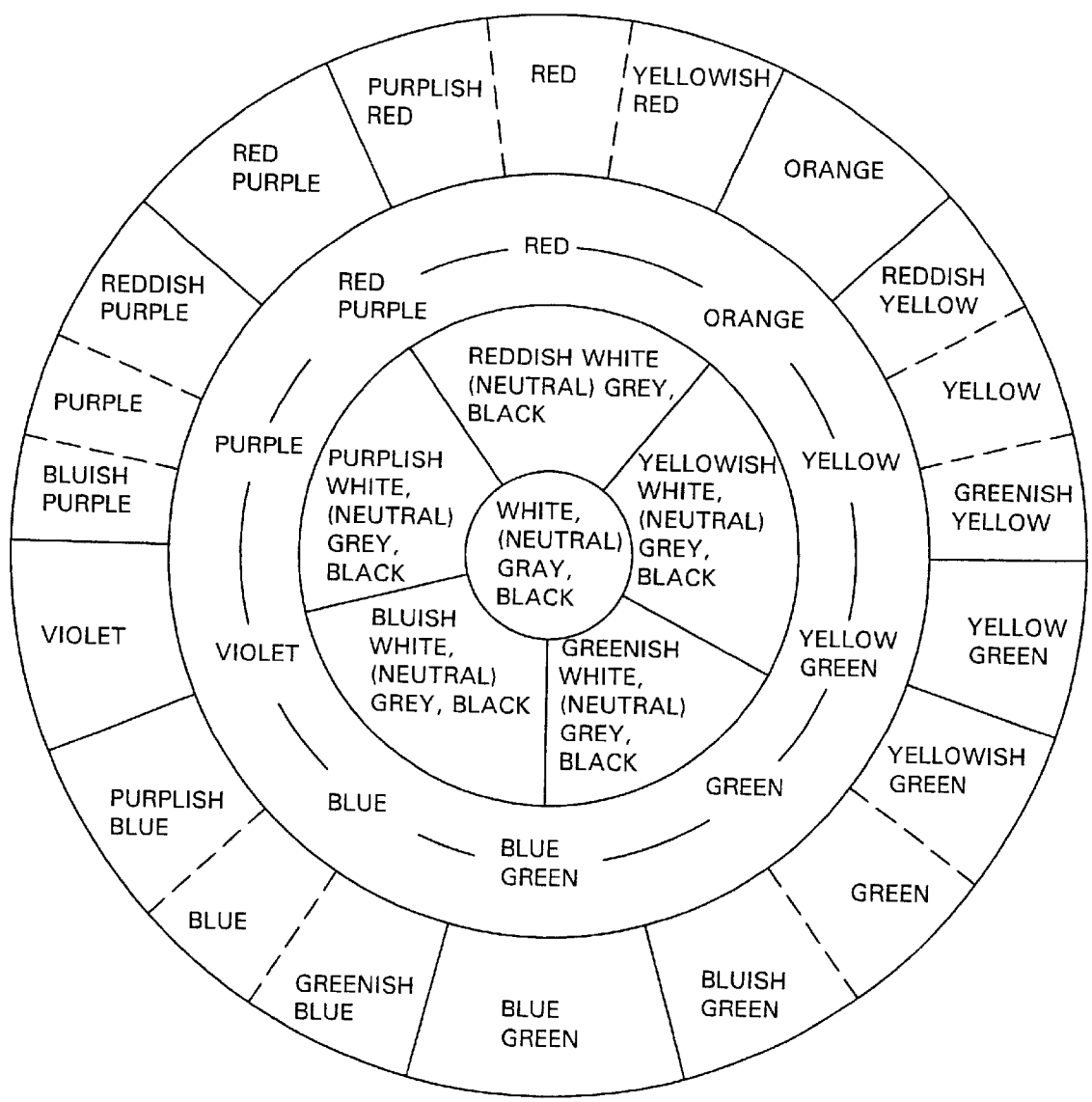
FIG. 9 is a drawing showing the correlation between modifiers concerning the hue of the JIS standards.
Figure 10:
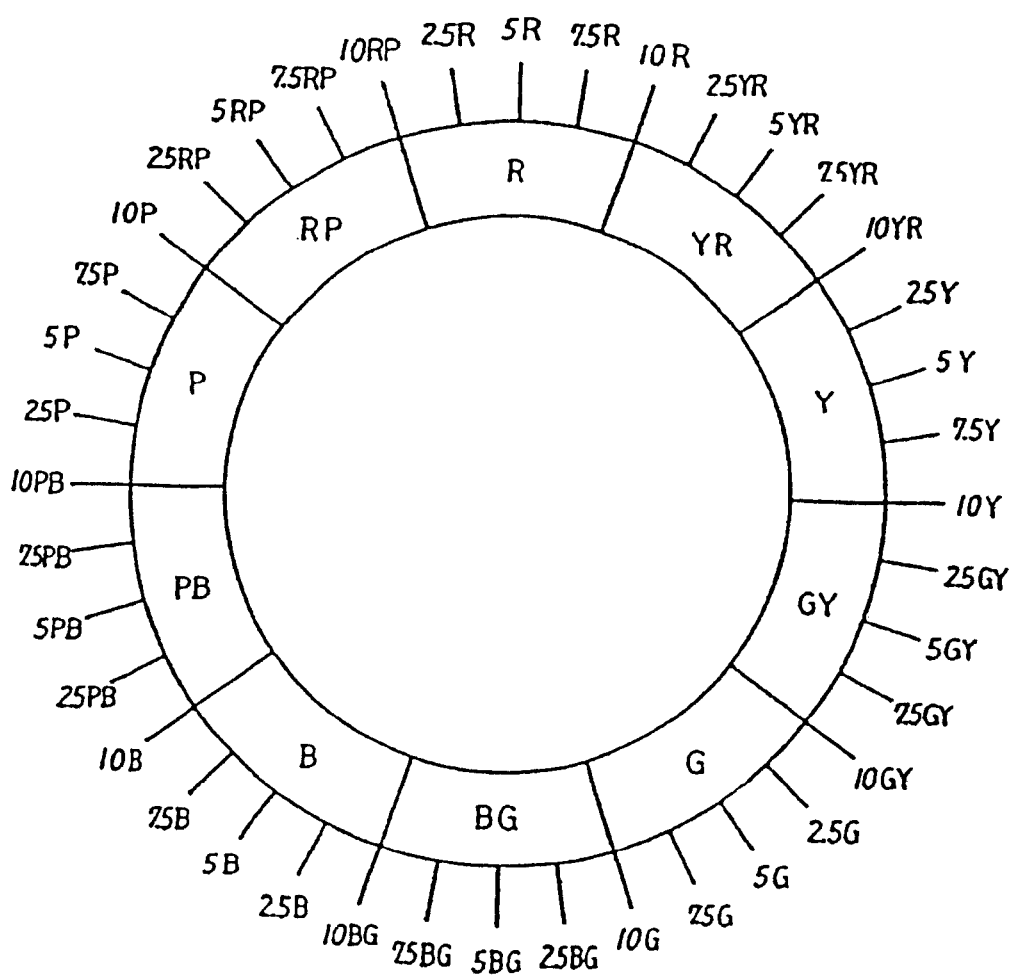
FIG. 10 is a drawing showing the division of hue ring of the JIS standards.

The hue names which are the ten types of the basic names of chromatic colors in the attributes of color perception are classified in compliance with the hue ring (Refer to FIG. 10 and FIG. 11) as shown in FIG. 9 (correlation between modifiers concerning hue), and the lightness and chroma are classified in compliance with the arrangement of lightness and chroma on a constant-hue plane (Refer to FIG. 12 and FIG. 13) as shown in FIG. 12 (Correlation between the lightness of achromatic colors, and lightness and chroma of chromatic colors).

In the invention, the abovementioned hue ring is classified into 360 degrees or into 20 steps (1 through 18), and hues are given to the respective basic chromatic colors, and the lightness is classified into 20 steps (1 through 20), wherein the lightness indication and chroma indication are given thereto.

Therefore, a brief description is given of the correlation between the lightness and chroma based on the JIS standards in compliance with FIG. 9 and FIG. 12. In the indication of FIG. 12, where red whose hue is zero is taken as an example, it becomes an achromatic color (white, gray, and black) when the chroma (abscissa) is 0, and it becomes red as the figure become larger, it becomes black where the lightness (ordinate) is zero in the case where the chroma is 0 (achromatic), and it becomes white as the figure becomes larger.

Where the chroma is of an intermediate figure or a large figure, it becomes [pale] or [light] when the lightness is large, it becomes [vivid] as the chroma becomes large, and it becomes [sober or darkish] as the chroma becomes small. These are common to the hue angles (that is, these are not limited to red, but are basically common to all the chromatic colors).

In FIG. 9, achromatic colors (white, gray and black) whose chroma is 0 are displayed at the center side, and chromatic colors are indicated at the periphery.

A description is given of the correlation between the abovementioned hue, lightness and chroma with reference to an example measurement shown in the embodiment. As shown in FIG. 7, the RGB data of white (white test sample) are R=231, G=228 and B=235, wherein the wavelengths of the three primary colors are considerably rich, and in a calculation expression of the HLS data described later, although the basic color is purple at (H=16), it becomes black at L=2 and S=5.

The RGB data of black (black test sample) is R=22, G=22, and B=17, wherein the wavelengths of the three primary colors are all slight, and although the basic color is yellow at (H=16). It becomes black at L=13 and S=16.

And, the RGB data of red (red test sample) are R=182, G=22, and B=29, wherein the wavelength of only red is considerably rich, and the basic color is red at H2 of hue and 357 degrees of a hue angle, and it becomes red of only the basic color at L=13 and S=16.

Also, a method for scaling and expressing the three attributes (hue, lightness and chroma) of color perception is regulated in the JIS standards (Z 8721).

In addition, the relationship between indications of Z 8721 and the systematic names of color (modifiers+basic color names, etc.,) is described in attached drawings 1 through 20 (only some of them are extracted and prepared in the embodiment of the invention) of Z8102.

And, in Z8721, indication symbols Hc, Vc and Cc of colors are obtained from three stimulus factors Yc and chroma coordinate xc and yc (one example of the calculation expression is introduced in terms of BASIC language).

However, in the JIS regulations, first, since devices and calculations become complicated as it is necessary to calculate the three stimulus factors, various types of simplified calculation expressions based on RGB data have been proposed. In the invention, a HLS color space which can be easily calculated based on RGB is employed, wherein hue, lightness and chroma are selected and determined in compliance with the JIS regulations.

Hereinafter, a description is given of the relationship between RGB, HLS and JIS regulations.

A color is composed of the three elements of RGB, and as shown in FIG. 8, a case where a color is expressed in terms of a three-dimensional space in which three elements of RGB are used as axes is called a "RGB color space", a specified color is positioned in the color space on the basis of the three values of RGB.

However, it is difficult to identify the color in the RGB space even though the color position is determined by three measured values.

On the contrary, color expression called a "Munsell hue ring" conventionally exists, by which the basic color names (hues) have been classified, and hue identification (color judgment) has been made normal.

And, the abovementioned JIS regulations are constituted on the basis of that color expression is carried out by adding the lightness and chroma to the Munsell hue ring.

Also, an HLS space (cylindrical HLS coordinate system) is provided as one example for expressing the hue, lightness and chroma, and FIG. 8 shows the relationship between the RGB color space and the HLS color space.

In addition, the reason why the HLS is employed is in that the coordinate system is cylindrical and is very near various types of JIS tables, wherein the format of data to be converted from RGB is not limited to the HLS, but if a type other than the HLS is employed, another calculation expression is employed, and it is necessary to prepare a table suited to the calculation expression.

Hereinafter, a description is given of a calculation conversion from RGB data of measured data to HLS data of calculated data, and how to obtain the hue, lightness and chroma.

First, a calculation expression to obtain a hue angle H is shown below. (Also, as regards processing of fractions, refer to an actual example described later).

Here, RGB, respectively, take figures from 0 through 255. (That is, after the RGB data measured by a color sensor 4$a$ are amplified by an operational amplifier 30, the data are analog-digital converted by an A/D converter, and are scaled in 256 graduations).

And, r, g, and b are figures which are obtained by dividing R, G, and B by 255, max is the largest figure of r, g, and b, and MIN is the smallest figure of r, g, and b.

Any one of the expressions (1), (2) and (3) is selected, depending on which element (among RGB data) is the maximum in the three primary colors, wherein a variable h is calculated.

Where R is the maximum among RGB data, $$h=(g-b)/(MAX-MIN) \tag{1}$$

Where G is the maximum among RGB data, $$h=2+(b-r)/(MAX-MIN) \tag{2}$$

Where B is the maximum among RGB data, $$h=4+(r-g)/(MAX-MIN) \tag{3}$$

After the variable h is calculated, H=h×60 is executed in order to indicate the variable h in the form of 360 degrees, and rightward turn or leftward turn is adjusted so that H becomes any integral number from 0 through 360.

$$\text{When } H \geq 0, H=H \tag{4}$$

(In the case of a rightward turn, the indication is made as it is).

$$\text{When } H<0, H=H+360 \tag{5}$$

(In the case of a leftward turn, rightward turn is indicated after 360 is added thereto).

Also, if MAX−MIN=0, H=0 is adopted.

A hue is selected from the hue angle H obtained as described above.

Figure 11:
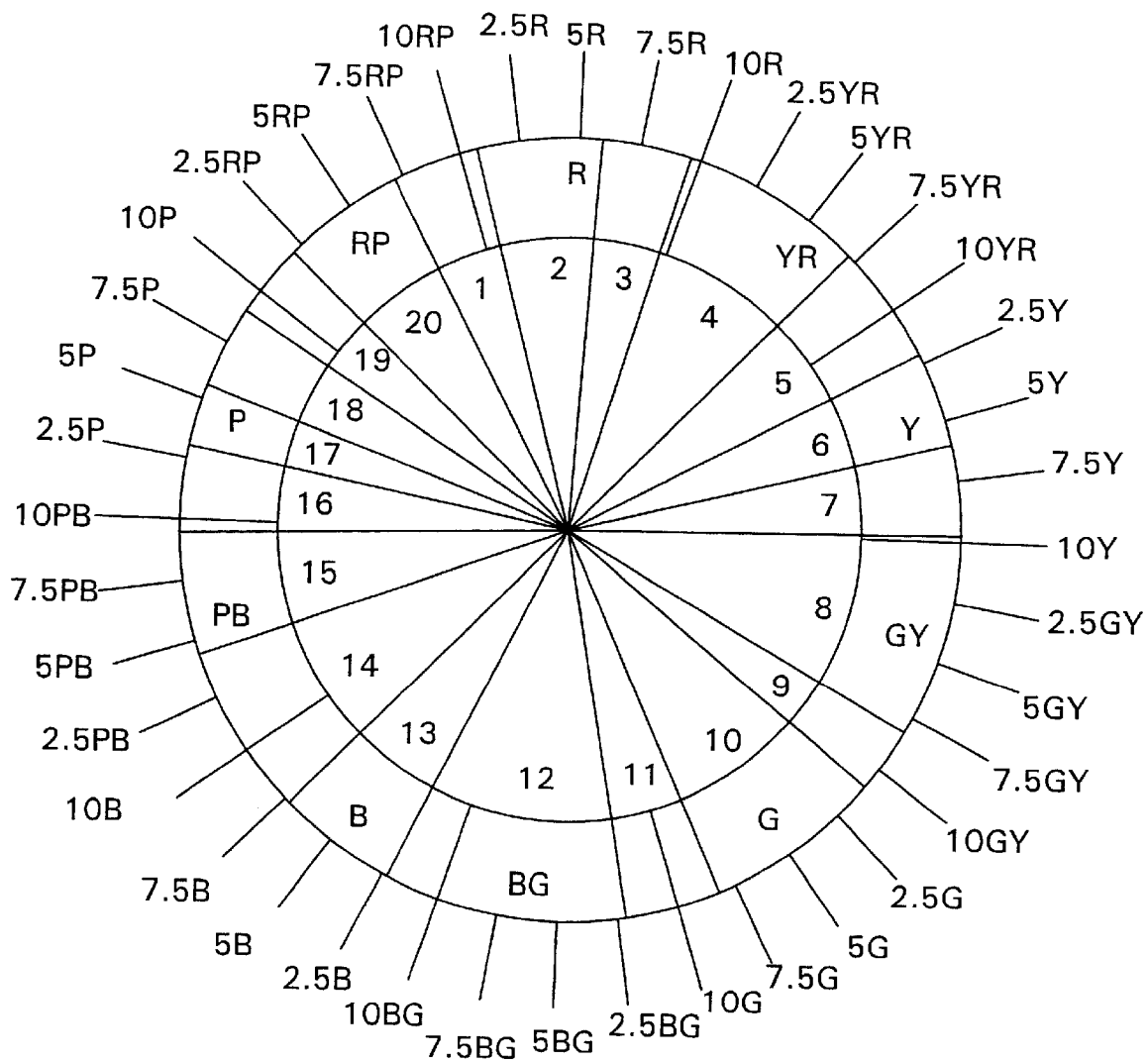
FIG. 11 is a drawing showing the relationship in classification of the hue rings between the JIS standards and the present invention.

FIG. 11 shows a color table number (Refer to FIG. 15), to which the HLS data are applied, added to a table (Refer to FIG. 10) of the division of hue ring of JIS-Z8721, and FIG. 15 shows the relationship between color table numbers and hue angles in the HLS.

And, the obtained hue angle H is applied to a table of the relationship in FIG. 15 to extract a color table number, and the color table number is applied to the hue ring of FIG. 11 to obtain hues (of chromatic colors).

Also, as regards achromatic colors, the abovementioned hues are not directly applied thereto, but these are determined by the relationship between the lightness L and chroma S.

Next, a calculation expression to obtain the lightness L is shown.

The calculation of the lightness L is executed so that it becomes figures from 0 through 20 in the expression (7) in order to display a variable l in 20 graduations after the variable l is obtained.

$$l=(MAX-MIN)/2 \quad (6)$$

$$L=\{100-(l\times 100)\}/5 \quad (7)$$

And, as shown in FIG. 16, the lightness 1 through 20 of the upper step is obtained from the calculation value L of the lower step.

A calculation expression to obtain the chroma S is shown below.

When obtaining the chroma S, any one of the expressions (8) and (9) is selected by a variable l in the calculation process of the lightness L, thereby calculating the variable S.

Where $l \leq 0.5$, $$s=(MAX-MIN)/(MAX-MIN) \quad (8)$$

Where $l > 0.5$, $$s=(MAX-MIN)/\{2-(MAX+MIN)\} \quad (9)$$

And, after the variable s is obtained, a calculation is further executed so as to secure a figure from 0 through 20 by an the expression (10) in order to indicate it in 20 graduations.

$$S=(s\times 100)/5 \quad (10)$$

Also, where MAX−MIN=0, s=0 is established.

And, as in the case of lightness L, the chroma 1 through is obtained from FIG. 16.

Figure 13:
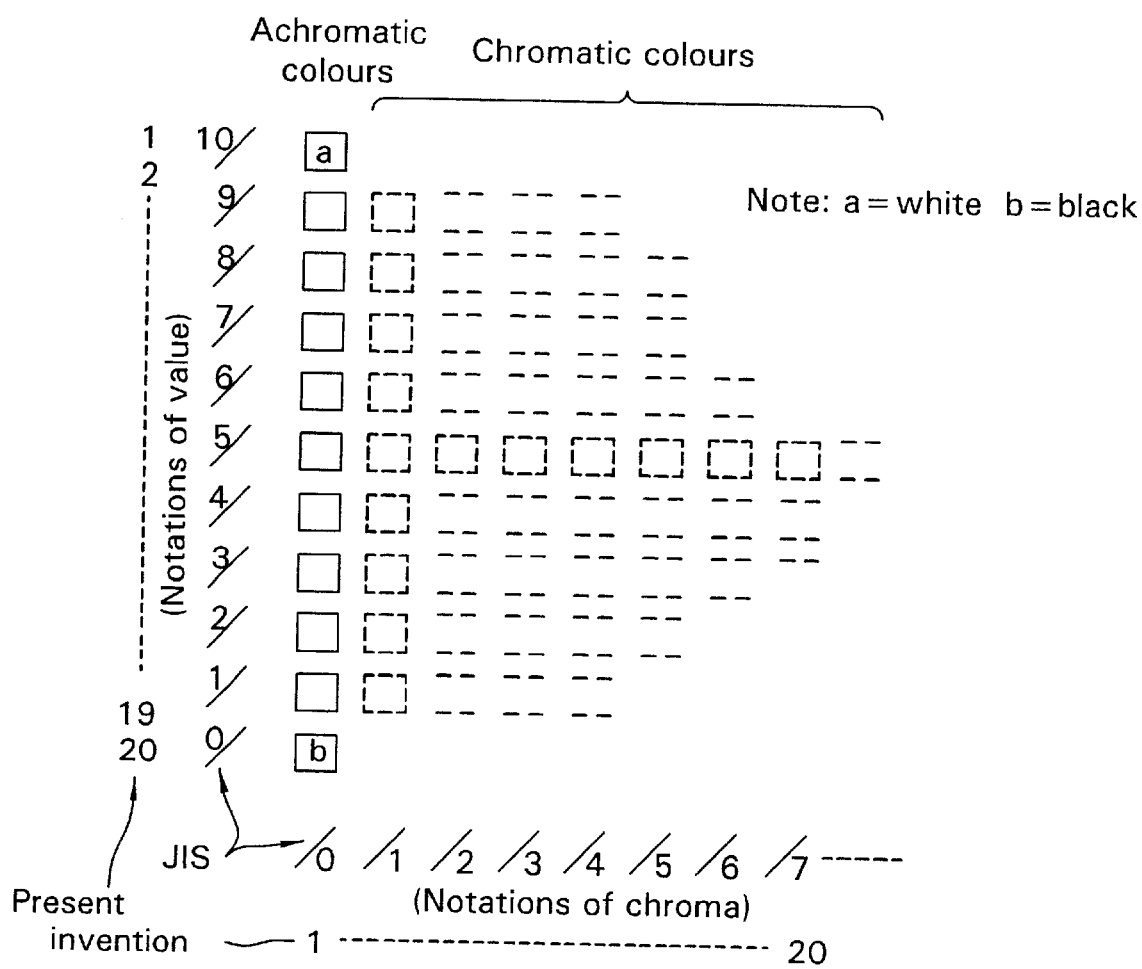
FIG. 13 is a drawing showing the arrangements of the lightness and chroma in constant-hue colors in accordance with the JIS standards and the invention.

Also, as shown in FIG. 13, although the lightness L and chroma S are scaled in 10 graduations in the JIS standards, these are scaled in 20 graduations in the HLS according to the invention.

And, availability of modifiers and achromatic colors are selected from the lightness L and chroma S obtained as described above.

Figure 14:
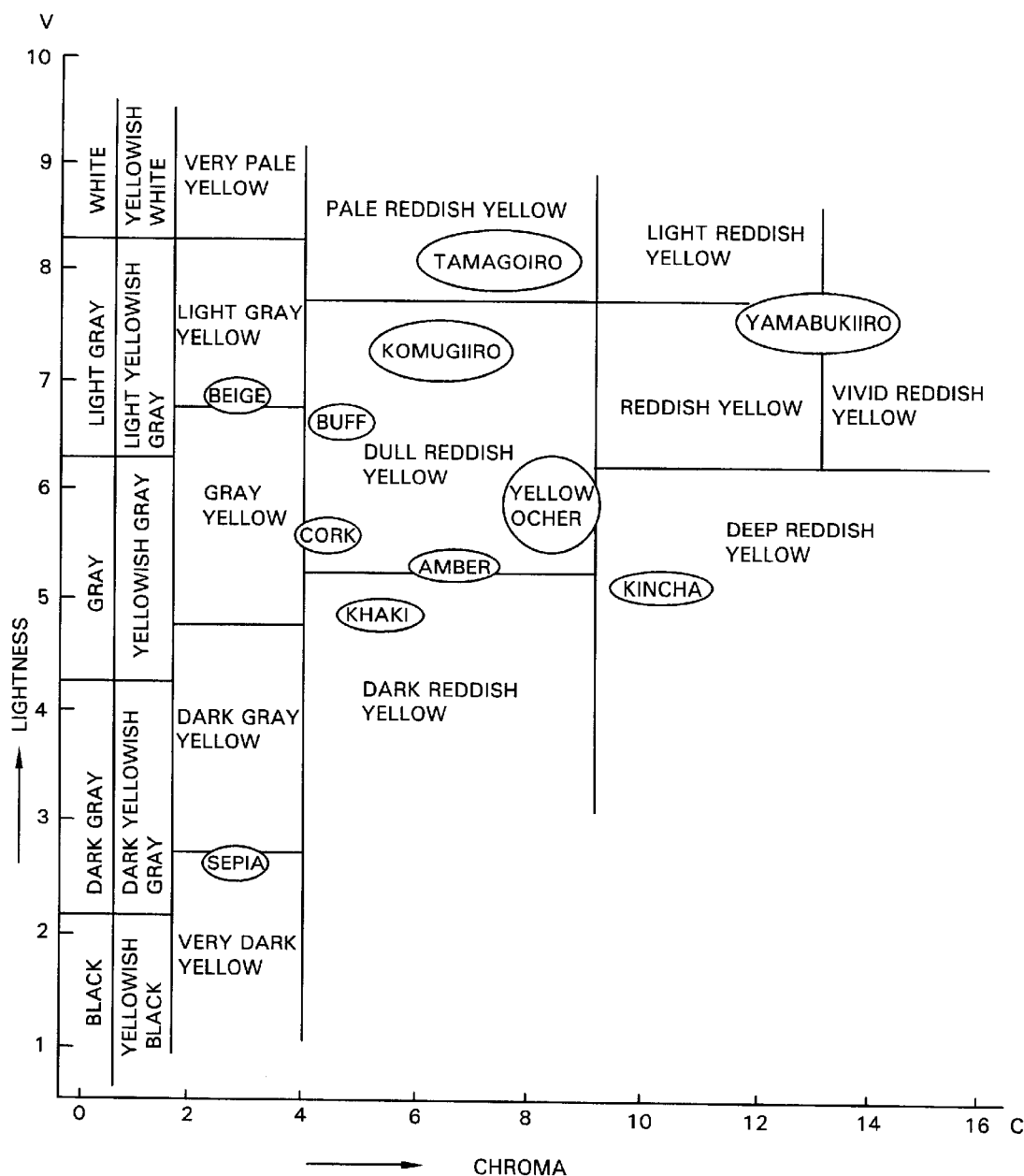
FIG. 14 is a drawing showing indication of colors in accordance with the three attributes of colors of the JIS standards and the relationship of the classified color names with regard to reddish yellow (sample 1, 2).

FIG. 17 is an L-S table concerning the hue in a color table 5, and the L-S table is linked with an attached drawing 5 (FIG. 14 in this specification) of JIS Z8102.

Subsequently, LS values in the table are extracted from respective figures concerning the lightness L of the ordinate and chroma S of the abscissa, wherein, based on the JIS attached drawing linked with the corresponding positions of the LS values, achromatic colors are selected when the chroma is 2 or less, and chromatic colors are selected when the chroma is 3 or more. Then, modifiers (including its availability) are selected from the chroma S and lightness L, wherein the color name is determined.

Also, the relationship between the LS figures and the color names is shown in FIG. 18.

A method for obtaining a color name on the basis of the HLS data calculated from the abovementioned R, G, B data is summarized as follows;

(1) The hue angle (H) is obtained, (2) The color table number is determined, (3) The hue (basic name of color) is determined (Achromatic colors are subjected to separate specifications), (4) Values of the lightness (L) and chroma (S) are determined, (5) Numbers are obtained from the L-S table, and (6) The color name is obtained.

Next, a description is given of a speaking system (peripheral outputting of a voice) after the color name is obtained.

Voice data regarding the basic name of colors, lightness, chroma and hue with respect to color names are separately stored in an EEP-ROM 33 of the controlling printed circuit board 6.

And, in response to the color name, only the data of the basic name of a color is extracted from the EEP-ROM 33 without extracting the voice data, for example, in a case of only the basic name of color, and if modifiers are provided, a plurality of voice data including the order thereof are extracted.

Also, the voice data extracted from the EEP-ROM 33 are converted from digital to analog by a D/A converter and is amplified by an operational amplifier 34, and the data are transmitted to a speaker 38 from which the data are peripherally outputted as voices.

Next, a description is given of two examples in which a color is identified based on the RGB data (one of which is a test sample 1 whose color name is gray, and the other of which is a test sample 2 whose color name is vivid reddish yellow).

The two examples are No. 549 ½ and No. 569 in the DIC color sample, both of which are reddish yellow. However, the lightness and chromas thereof are different from each other, and these are examples in which an achromatic color and a chromatic color are judged.

In addition, the following actual example shows an example of processing of fractions. However, the position to which processing of fractions is applied may be adequately changed, and in this case it may be adequately corrected.

RGB data obtained by irradiating light to the test sample 1 (No. 549 ½ in the DIC sample) and receiving the light therefrom are R=126, G=121 and B=104.

Since R is the maximum, h=0.772727 (Round it off to six decimal places).

Since H≧0, H=46 (disregard all the decimals).

Therefore, it is understood from FIG. 15 that the color table number is 5.

From the expression (6), l=0.45098 is obtained (when calculating L, round it off to two decimal places, when calculating s, round it off to five decimal places).

From the expression (7), L=11 is obtained, and it is found from FIG. 16 that the lightness is 12.

Since $l \leq 0.5$, s=0.0956522 is obtained from the expression (8) (round it off to seven decimal places, and disregard all the decimals when calculating S (when calculating s×100)), and S=1 (disregard all the decimals) is obtained from the expression (10).

It is found from FIG. 16 that the chroma is 2.

Based on the above description, H=46, Hue=5, light(L)= 12, chroma(S)=2 are obtained.

If L=12 and S=2 are applied to the L-S table (FIG. 17) of hue=5, an LS value=3 can be obtained, and this indicates gray.

Also, this color name ([gray]) is composed of only the basic color name, and one example of types of signals in a computer is (0,0,N) (as shown in FIG. 4b, N=gray).

RGB data obtained by irradiating light to the test sample 2 (No. 569 in the DIC sample) and receiving light therefrom is R=255, G=212 and B=0.

Since R is the largest, h=0.831373 (round it off to six decimal places) is obtained from the expression (1).

Since H≧0, H=49 is obtained (disregard all the decimals) from the expression (4). Then, it is found from FIG. 15 that the color table number is 5.

=0.5 (having no fractions) is obtained from the expression (6), and L=10 is obtained from the expression (7). Then, it is found from FIG. 16 that the lightness is 11.

Since ≦0.5, s=1 (having no fractions) is obtained from the expression (8). S=20 (disregard all the decimals) is obtained from the expression (10). Then, it is found from FIG. 16 that the chroma is 20.

Based on the above description, H=49, hue=5, lightness (L)=11, and chroma=20 are obtained. If L=11 and S=20 are applied to the L-S table (FIG. 17) of hue=5, an LS value=22 can be obtained.

This indicates [vivid reddish yellow] (Refer to FIG. 18).

Also, this color name ([vivid reddish yellow]) is a hue modifier (as shown in FIG. 4(a), FIG. 5 and FIG. 6, a modifier vv of the lightness and chroma vivid, a modifier r=reddish, and basic color y=yellow) as one example of types of signals in a computer.

Also, in the JIS attached drawing (FIG. 14 in the present specification) and the L-S table of FIG. 17 linked to said drawing, some colors are not indicated, and, in the calculated HLS data, some colors correspond to the margin, so that some corrections are made to obtain the color names.

As a correction method, one or both of lightness and chroma is defined as a standard to determine the LS value of a color in the margin.

Next, a proofing method shall be described.

The abovementioned conversion of the RGB data into HLS data is based on digital data of the three primary colors being in 256 (0–255) gradations.

And, due to the use of the color identifying device, change in the power source (for example, lowering in the accumulated amount of electricity and lowering in output electricity (voltage and current)), change in the temperature for use, and aging deterioration occur, so that the RGB data is not always detected in the 256 gradations.

Therefore, based on the RGB data of a proof test sample such as a black test sample or a white test sample to be generally used, proofing of the data of the three primary colors at the time of use of the device is carried out.

That is, if the measured data of the white test sample 24 and black test sample 23 coincide with the reference RGB data (231, 228, 235) and (22, 22, 17), proofing is unnecessary. However, in accordance with the RG data obtained from the white and black test samples, the RGB data of an object is proofed by means of proportional distribution and converted into HLS, whereby the color identification is made.

For example, proofing is made to judge which side of the small value side, middle value side, or large value side, one or both of the measured RGB data of the white and black test samples 23 and 24 is inclined to in comparison with the abovementioned reference RGB data.

As an example, for each of R, G, and B, if the measured data is at the small value side, a coefficient for upper value correction is set, if the measured data is at the middle value side, correction is made for a value above 123 and correction is made for a value under 122, and if the measured value is at the large value side, lower value correction is made.

These corrections are made immediately before the measurement of the object, whereby accurate RGB data, HLS data, and color identification are achieved.

Also, (255, 255, 255) is the basis of white, and (0, 0, 0) is the basis of black, however, the original data (231, 228, 235) and (22, 22, 17) of the black test sample 23 and white test sample 24 loaded to the measurement base plate 21 is defined as a reference data for proofing.

Furthermore, the black test sample 23 and white test sample 24 are used as proof test samples of specific colors to be used for self-proofing, however, these samples can be properly changed.

For example, it is considered that, when black test sample 23 and white test sample 24 whose measured data is (0, 0, 0) or (255, 255, 255) are employed, two proof test samples become necessary. However, if a proof test sample of other measured data such as (22, 22, 17) or (231, 228, 235) of the embodiment are employed, three values of RGB exist, so that one proof test sample is enough.

In addition, in place of the black test sample 23 or white test sample 24, one to three of the three-primary color samples can be employed, or a sample of an optional specified color can be employed.

That is, as far as the measured data of a proof test sample is stored as a reference data and comparison with this is possible, any color can be selected for the proof test sample.

When the three-primary color samples are employed, the data of one of the three samples is prominent, so that proofing is carried out based on the data of the maximum value among the three, or in the case where 1 or 2 samples are employed, proofing is carried out based on the data of the maximum value and the data of the relative two low values.

Although particular preferred embodiments of the invention have been disclosed in detail for illustrative purposes, it will be recognized that variations or modifications of the disclosed apparatus, including the rearrangement of parts, lie within the scope of the present invention.

What is claimed is:

1. A color identifying device for identifying a color of an object, said device comprising:

a housing defining therein a measuring aperture;

a measuring portion disposed within said housing and including a white light source which irradiates white light onto the object through said measuring aperture, and three primary color light receiving elements which receive light reflected from the object through said measuring aperture;

a proofing device disposed within said housing between said measuring portion and said measuring aperture, said proofing device including a disk having a test sample of a specified color and a measuring window, said disk being mounted for intermittent rotation within said housing relative to said measuring aperture;

a color identifying device which judges colors by comparing data measured by said light receiving elements with stored reference data; and an output device which outputs colors judged and identified by said color identifying device in the form of a voice.

2. The color identifying device of claim 1 wherein said proofing device permits automatic proofing of the color-identifying accuracy of said device by said measuring portion by rotating said disk and moving said test sample between said measuring portion and said measuring aperture, and comparing data measured from said test sample by said measuring portion with stored reference data pertaining to said test sample.

3. The color identifying device of claim 2 wherein said proofing device permits automatic measuring of a color of the object by rotating said disk and moving said measuring window between said measuring portion and said measuring aperture, and comparing data measured from the object by said measuring portion with stored reference data.

4. The color identifying device of claim 3 further including a switch assembly which when actuated activates said measuring portion and said proofing device to allow identification of the color of the object by said device.

5. The color identifying device of claim 4 wherein said color identifying device comprises control circuitry.

6. The color identifying device of claim 5 further including a power source disposed within said housing for powering said device.

7. The color identifying device of claim 6 wherein said power source is a battery, and said housing defines a box-shaped structure configured to mount said battery within said housing.

8. The color identifying device of claim 1 wherein HLS data are calculated from RGB data of the measured data and are compared with the stored reference data.

9. The color identifying device of claim 1 wherein said light receiving elements comprise photoelectric converting elements having sensitivity with respect to the three primary colors.

10. The color identifying device of claim 9 wherein said photoelectric converting elements comprise photo diodes provided with three types of filters RGB.

11. The color identifying device of claim 2 wherein said test sample comprises one of a black test sample and a white test sample.

12. The color identifying device of claim 2 wherein said proofing device includes three of said test samples disposed on said disk, and said test samples respectively correspond to the three primary colors.

13. The color identifying device of claim 1 wherein said output device includes a speaker for externally outputting a voice which identifies the color of the object as identified by said color identifying device.

14. The color identifying device of claim 1 wherein said output device includes an earphone for externally outputting a voice which identifies the color of the object as identified by said color identifying device.

15. The color identifying device of claim 4 wherein said color identifying device includes a printed circuit board mounted within said housing, said switch assembly includes a switch mounted on said circuit board and a base plate, said base plate is mounted for rotation within said housing about a first axis and defines a gear portion at an outer circumferential portion thereof, an actuating portion engageable with said switch, and a switch portion which projects outwardly from said housing for manipulation by a user, said disk is mounted for rotation within said housing about a second axis spaced from said first axis and a gear is fixed to said disk for movement therewith, said measuring window and said test sample are circumferentially spaced from one another along said disk, said circuit board includes a timing sensor which cooperates with said disk so as to sense the positions of said test sample and said measuring window, said gear portion of said base plate is engaged with said gear of said disk, whereby upon actuation of said switch portion by a user, said disk rotates in response to rotation of said base plate to cause sequential movement of said test sample and said measuring window towards said measuring aperture and said switch is actuated by said actuating portion.

* * * * *